United States Patent [19]
Sumiya

[11] Patent Number: 5,800,424
[45] Date of Patent: Sep. 1, 1998

[54] APPARATUS FOR USE IN OPERATING UPON A CORNEA

[75] Inventor: Toshifumi Sumiya, Aichi, Japan

[73] Assignee: Nidek Co., Ltd., Japan

[21] Appl. No.: 738,785

[22] Filed: Oct. 29, 1996

Related U.S. Application Data

[63] Continuation-in-part of Ser. No. 466,430, Jun. 6, 1995, abandoned.

[30] Foreign Application Priority Data

Oct. 31, 1995 [JP] Japan .................. HEI 7-308441
Jun. 24, 1996 [JP] Japan .................. HEI 6-166231

[51] Int. Cl.$^6$ ............................................ A61N 5/06
[52] U.S. Cl. ................................................ 606/4
[58] Field of Search ...................... 606/4, 5, 6, 10, 606/11, 12

[56] References Cited

U.S. PATENT DOCUMENTS

| | | |
|---|---|---|
| 4,953,969 | 9/1990 | Fedorov . |
| 4,994,058 | 2/1991 | Raven et al. .................. 606/4 |
| 5,445,633 | 8/1995 | Nakamura et al. .................. 606/5 |
| 5,470,329 | 11/1995 | Sumiya .................. 606/4 |
| 5,569,238 | 10/1996 | Shei et al. .................. 606/4 |

FOREIGN PATENT DOCUMENTS 0 296 982  12/1988  European Pat. Off. .
64-86968   3/1989   Japan .
2-84955    3/1990   Japan .
4-33220    6/1992   Japan .

*Primary Examiner*—Jennifer Bahr
*Assistant Examiner*—Sonya Harris-Ogugua
*Attorney, Agent, or Firm*—Finnegan, Henderson, Farabow, Garrett & Dunner, L.L.P.

[57] ABSTRACT

An apparatus for use in operating upon a cornea of an eye comprises a light delivery optical system for delivering an ultraviolet laser beam emitted from a laser source onto the cornea, a diaphragm with an aperture, disposed in the light delivery optical system, for restricting an irradiation area of the laser beam, a device for shifting the laser beam with respect to an optical axis of the light delivery optical system, a device for rotating the laser beam about the optical axis of the light delivery optical system at each shifting position to ablate the cornea circularly, a device for inputting information necessary for determining the shape of the postoperation cornea, a device for determining ablation amount at each shifting position of the laser beam by the beam shifting device, based on the information input through the input device, and a device for controlling the laser source and action of the beam rotating device based on the ablation amount determined by the ablation amount determining device at each shifting position, wherein the laser beam ablates the cornea of the eye to correct ametropia including hypermetropia.

23 Claims, 15 Drawing Sheets

PRIOR ART

FIG. 9

| SHIFTING POSITION | a | b | c | d | e | f | g | h | i |
|---|---|---|---|---|---|---|---|---|---|
| SHIFTING DISTANCE FROM ROTATION AXIS (mm) | 1.4 | 2.8 | 4.2 | 5.6 | 7.0 | 8.4 | 9.8 | 11.2 | 12.6 |

FIG. 14

| SHIFTING POSITION | a | b | c | d | e | f | g | h | i |
|---|---|---|---|---|---|---|---|---|---|
| RATIO OF TIME OF LASER BEAM IRRADIATION | 1 | 4 | 9 | 16 | 25 | 36 | 49 | 64 | 81 |

SHIFTING POSITION (c)

SHIFTING POSITION (d)

SHIFTING POSITION (e)

SHIFTING POSITION (f)

SHIFTING POSITION (g)

SHIFTING POSITION (h)

SHIFTING POSITION (i)

FIG. 15(a)

ABLATION CONDITIONS (1)

| | TIME OF LASER IRRADIATION (sec) | | | | | | | | | | HIGH VOLTAGE OF LASER (HV) |
|---|---|---|---|---|---|---|---|---|---|---|---|
| | a | b | c | d | e | f | g | h | i | Total | |
| A | 1 | 4 | 9 | 16 | 25 | 36 | 49 | 64 | 81 | 285 | 27 KV |
| B | 2 | 8 | 18 | 32 | 50 | 72 | 98 | 128 | 162 | 570 | |
| C | 0.5 | 2 | 4.5 | 8 | 12.5 | 18 | 24.5 | 32 | 40.5 | 142.5 | |
| D | 1.5 | 6 | 13.5 | 24 | 37.5 | 54 | 73.5 | 96 | 121.5 | 427.5 | |

FIG. 15(b)

ABLATION CONDITIONS (2)

| | TIME OF LASER IRRADIATION (sec) | | | | | | | | | | POSITION OF PROJECTIVE LENS | ABLATION SIZE (DIAMETER) | LASER ENERGY |
|---|---|---|---|---|---|---|---|---|---|---|---|---|---|
| | a | b | c | d | e | f | g | h | i | Total | | | |
| E | 1 | 4 | 9 | 16 | 25 | 36 | 49 | 64 | 81 | 285 | FOR ø 9 | ø 9 | 130 mJ |
| F | 2 | 8 | 18 | 32 | 50 | 72 | 98 | 128 | | 408 | | ø 6.5 | |
| G | 3 | 12 | 27 | 48 | 75 | 108 | 147 | 192 | | 612 | | | |
| H | 0.5 | 2 | 4.5 | 8 | 12.5 | 18 | 24.5 | 32 | | 102 | | | |

FIG. 16

| ABLATION CONDITIONS | MEASURED DATA BY LENSMETER |
|---|---|
| A | 7.76 D |
| B | 15.43 |
| C | 3.85 |
| D | 12.88 |
| E | 4.40 |
| F | 9.84 |
| G | 14.88 |
| H | 2.40 |

I : INCLUDING THE SHIFTING POSITION (i)

II : NOT INCLUDING THE SAME

B−B' Cross-sectional profiles

APPARATUS FOR USE IN OPERATING UPON A CORNEA

This application is a Continuation-In-Part of U.S. Ser. No. 08/466,430, filed Jun. 6, 1995 now abandoned in the name of Toshifumi SUMIYA.

BACKGROUND OF THE INVENTION

1. Field of the Invention

The present invention relates to an apparatus for use in operating upon a cornea of an eye to correct ametropia by operating a laser beam, and more particularly relates to an apparatus so as to correct hyperopia or myopia by changing a curvature radius of a cornea of the hyperopia or myopia eye, and also being suitable for correcting astigmatism to change the curvature of the cornea in a certain direction.

2. Description of Related Art

Recently a method is known of correcting ametropia of an eye by eliminating a part of the surface of a cornea by operating a laser beam, and thereby changing the curvature of the cornea. This is called Photo-refractive Keratectomy. This method is actually utilized for only correction of myopia, and hardly utilized for correction of hypermetropia due to the following reason.

In the case of correcting myopia, as shown in FIG. 1(a), it is enough to remove the surface part of the cornea deeply at its center and slightly at its periphery, the removed part being convex lens shaped. To remove the cornea as mentioned above, a regular diaphragm with a variable circular aperture is utilized to change an ablation area by the laser beam on the cornea, thereby correction of myopia may be relatively easily achieved.

In the case of correcting hypermetropia, contrarily, as shown in FIG. 2(a), the surface of a cornea Ec has to be removed slightly at its center and deeply at its periphery, the removed part being concave lens shaped. Accordingly, removing the surface of the cornea in such a way is a difficult operation for a standard diaphragm in that an aperture diaphragm must cut the laser beam off in its center part and also vary the radius size of aperture.

To control the diaphragm utilized for correction of hypermetropia, several methods have already been proposed. For instance, Japanese Patent Publication (Kokoku) No. 4(1992)-33220 based on the United Kingdom Patent Application No. GB 8606821 (Applicant: Summit Technology, Inc.,) which corresponds to U.S. Pat. No. 4,994,058, declares a method of ablating the surface of a cornea into a concave lens shape by using a special mask (see FIG. 3). The mask used in this method has resistance to a laser beam, which is suitable for a predefined shape or profile, and is constituted so that its center part may absorb more and transmit less of a laser beam, and its peripheral part may absorb less and transmit more of a laser beam. The profile is created by varying the thickness or the composition of the mask. When a laser beam is passed through the mask to irradiate the cornea, a part of the laser beam is selectively absorbed and the other part is transmitted through the mask and delivered to the cornea, so that the surface of the cornea is removed in the shape of a concave lens.

Japanese Patent Laid-Open (Kokai) No. 64(1989)-86968 based on French Patent Application No. FR 8708963 corresponding to European Patent Publication No. 0 296 982 (applicant; International Business Machines Corporation) proposes another method of irradiating a laser beam while rotating a diaphragm with a lobe-shaped aperture (see FIG. 4). The lobe-shaped aperture of the diaphragm is formed in a predefined shape. A plurality of the images of the lobe of the laser beam passed through the aperture of the diaphragm are intermittently overlapped on the cornea to eliminate the surface of a cornea by thickness necessary to correct ametropia, accordingly, the curvature of the cornea is changed according to eliminated part of the cornea. The aperture of the diaphragm utilized for correction of hypermetropia is formed in a lobe shape having large width at a part corresponding to the peripheral part of the cornea, so that the periphery of the cornea may be ablated more than the center part of the cornea.

A similar method to the above Japanese Patent Laid-Open (Kokai) No. 64(1989)-86968 is described also in Japanese Patent Laid-Open (Kokai) No. 2(1990)-84955, the title of which is device for correcting ocular refraction anomalies, based on U.S.S.R. Patent Application No. SU 4457772 which corresponds to U.S. Pat. No. 4,953,969.

However, the above prior methods to correct hypermetropia have the following problems.

In the former method using a special mask, the shape of the mask varies according to corneal curvature and correction refractive power of the eye to be treated, accordingly, a number of masks must be ready in various shapes for every curvature and correction refractive power of the pre-operation eye. Because the thickness of the eliminated cornea depends on the shape of the mask, precision of the shape of the mask is an important factor in ametropia correction, and manufacture of the mask becomes difficult.

In the latter method of displacing images of the lobe of the aperture, the shape of the required aperture is different according to curvature and correction refractive power of the pre-operation cornea, similarly as in the above method, causing a problem requiring various kinds of apertures.

On the other hand, in the case of the correction of astigmatism, as the correction operation by this PRK method is mostly occupied for the correction of myopia astigmatism, this method is hardly utilized for the correction of hyperopia astigmatism. As the reason, concerning the correction of myopia astigmatism, as shown in FIG. 1(b), it is enough to remove the surface of a cornea deeply at its center only in a certain direction and slightly at its periphery, the removed part being cylindrical convex lens shaped, therefore, it is performed comparatively easy by changing an ablation area of the laser beam by using a diaphragm with a variable aperture, in the case of correcting hyperopia, contrarily, as shown in FIG. 2(b), the surface of a cornea has to be removed slightly at its center in a certain direction and deeply at its periphery, the removed part being cylindrical concave lens shaped. In the hypermetropia astigmatism correction, it needs a difficult control for a standard diaphragm such that a aperture diaphragm must cut laser beam off in its center part and also vary the width size of aperture.

SUMMARY OF THE INVENTION

The present invention has been made in view of the above circumstance and has a purpose for overcoming the above problems and to provide an apparatus for operating on a cornea to correct ametropia, capable of correcting hypermetropia or myopia, with a simple construction and without needing a number of masks or diaphragms.

It is another object of the present invention to provide an apparatus for operating on a cornea to correct ametropia, capable of correcting myopia or hypermetropia astigmatism easily with a simple construction.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, there is provided an apparatus for use in operating upon a cornea comprising a light delivery optical system for delivering an ultraviolet laser beam emitted from a laser source onto the cornea, a diaphragm with an aperture, disposed in the light delivery optical system, for restricting an irradiation area of the laser beam, means for shifting the laser beam with respect to an optical axis of the light delivery optical system, means for rotating the laser beam about the optical axis of the light delivery optical system at each shifting position to ablate the cornea circularly, means for inputting information necessary for determining the shape of a post-operation cornea, means for determining the ablation amount at each shifted position of the laser beam by the beam shifting means, based on the information input through the input means, and means for controlling the laser source and action of the beam rotating means based on the ablation amount determined by the ablation amount determining means at each shifted position, wherein the laser beam ablates the cornea of the eye to correct ametropia.

In another aspect of the present invention, the apparatus for use in operating a cornea comprises a light delivery optical system for delivering an ultraviolet laser beam emitted from a laser source onto the cornea, a diaphragm with an aperture, disposed in the light delivery optical system, for restricting an irradiation area of the laser beam, means for shifting the laser beam with respect to an optical axis of the light delivery optical system, means for rotating the laser beam about the optical axis of the light delivery optical system, means for inputting information necessary for determining a shape of a postoperation cornea, first memory means for storing the relation between a spherical correction amount and an ablation amount at each shifted position that is necessary for correcting a spherical refractive power by irradiating and rotating the laser beam about the optical axis of the light delivery optical system at each shifting position to ablate the cornea circularly, and then accumulating circular ablation, second memory means for storing the relation between a cylindrical correction amount and the ablation amount at each shifting position so as to correct the cylindrical refractive power by accumulating the irradiation of laser beam which is shifted by the beam shifting means, under the condition that the laser beam is rotated by said beam rotating means so that the shifting direction of the shifting means may coincide with the astigmatism axis direction, means for determining the ablation amount at each position of the laser beam based on the input information by the inputting means and the first memory means and the second memory means, and means for controlling movement of a laser source and the beam rotating means at each shifted position based on the ablation amount determined by the ablation amount determining means.

According to the present invention, a simply constructed apparatus enables ablation on a cornea in a desired shape to correct hypermetropia.

Also, according to the present invention, simply constructed apparatus enables optional ablation shape in a certain direction, rendering it possible to correct hypermetropia astigmatism as well as myopia astigmatism.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings:

FIG. 9 is a table of a displacement distance of a plane mirror 3 from a rotation axis denoted by L as shown in FIG. 5;

FIG. 14 is a table of a combination of each position of the mirror and corresponding irradiation time of the laser beam in order to ablate PMMA plate to form into a convex lens shape;

FIGS. 15 (a) and (b) are tables—of ablation conditions;

FIG. 16 is a table of measured data by a lensmeter for every ablation condition[s] shown in FIG. 15;

DETAILED DESCRIPTION OF THE PREFERRED EMBODIMENTS

Figure 5:
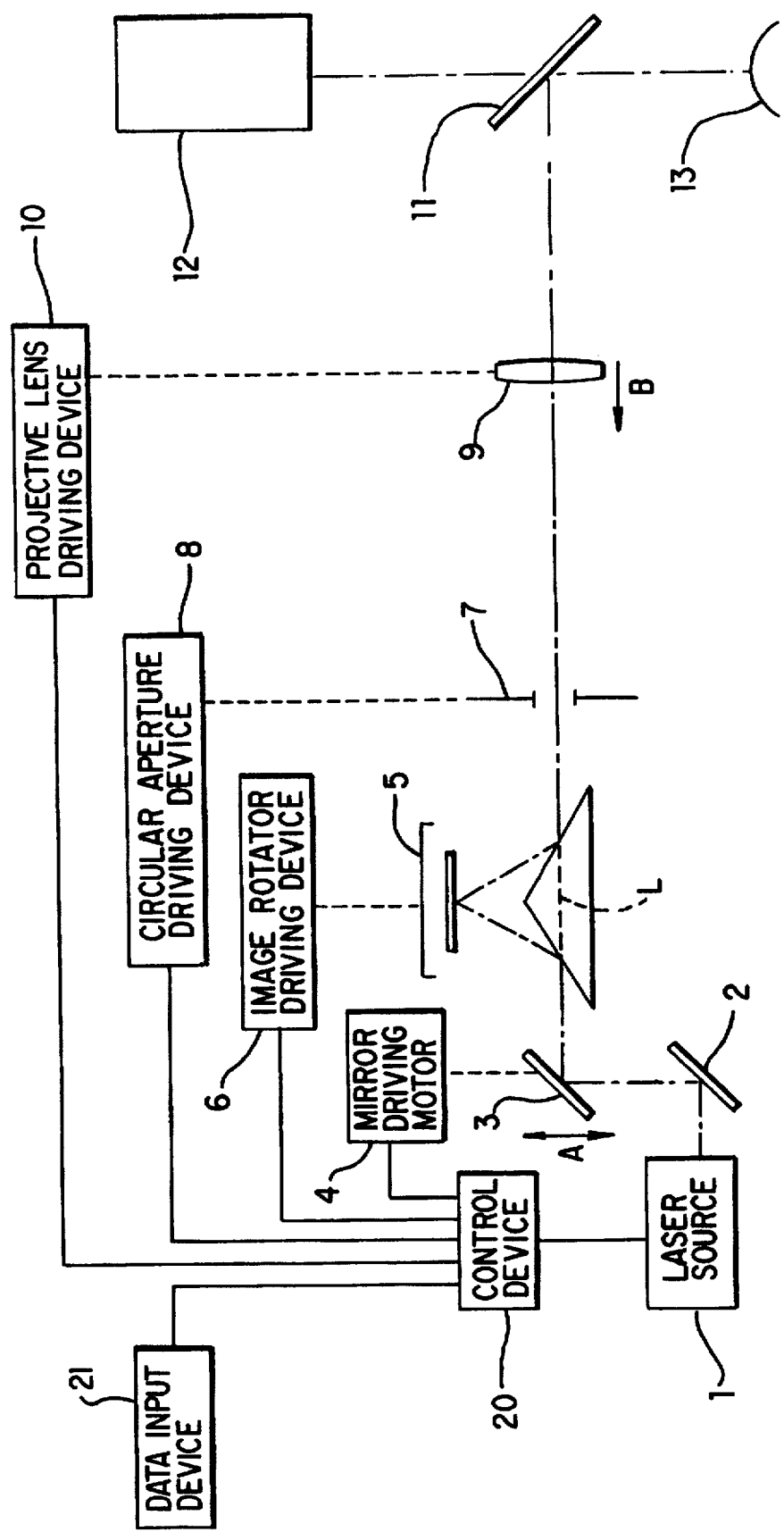
FIG. 5 is a schematic diagram for explaining the arrangement of an optical system and a control system in the embodiment of the present invention.

A detailed description of preferred embodiments of an apparatus for operating on a cornea embodying the present invention will now be given referring to the accompanying drawings. FIG. 5 shows a schematic arrangement of an optical system and a control system of the apparatus in the describes embodiment.

Figure 6:
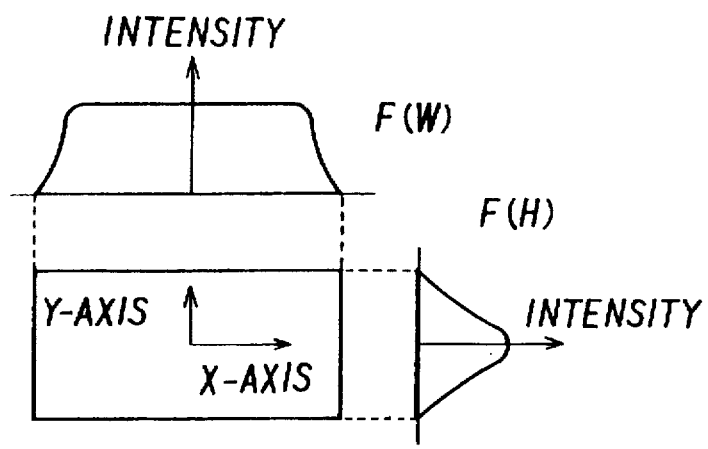
FIG. 6 is a schematic diagram of a typical form of a laser beam emitted from an excimer laser.

Numeral 1 is a laser source. In the present embodiment an excimer laser source having a wavelength of 193 nm is used as a laser. An excimer laser beam from the laser source 1 is a pulse wave, which has typically a sectional profile as shown in FIG. 6, i.e., a substantial uniform intensity distribution F(W) in a horizontal direction (x-axis direction) of the laser beam and a Gaussian intensity distribution F(H) in the vertical direction (y-axis direction).

Plane mirrors 2 and 3 serve for deflecting the laser beam emitted from the laser source 1, namely, at right angles upward by the mirror 2 and then in a horizontal direction by the mirror 3. The mirror 3 is movable parallel to the arrow denoted by A through a mirror driving motor 4 which is a pulsed motor, having gears and cams and other parts. In accordance with movement of the mirror 3 in the direction of the arrow A, the laser beam emitted from the laser source 1 is translated in a Gaussian distribution direction so that the laser beam is shifted from an optical axis denoted by L of the light delivery optical system. The image rotator 5 is driven to rotate about the optical axis L as a center by an image rotator driving deice 6, thereby rotating the laser beam as displaced about the optical axis.

Numeral 7 is a circular diaphragm for limiting an ablation area on a cornea 13, an aperture diameter of which is variable by an aperture driving device 8. The optical system is further provided with a projective lens 9 and a projective lens driving device 10. The projective lens 9 is for projecting an image of the aperture of the diaphragm 7 on the cornea 13, its projective magnification being about a quarter and movable in an arrow B along an optical axis by the driving device 10 to change size of an image of the aperture to be projected on the cornea 13.

Laser beam reflected by the plane mirror 3 is further reflected and rotated at the image rotator 5, then is passed through the aperture of the diaphragm 7 and the projective lens 9, and reflected at right angle downward by a dichroic mirror 11 to fall on the cornea 13.

Numeral 12 is an observing optical system of a binocular microscope for use in surgical operation, which is constructed of a right and a left optical systems disposed such that the dichroic mirror 11 is put therebetween. Since such a binocular observing optical system is available as various kinds on the market and the construction itself is not much concerned with the present invention, the description is omitted herein.

The cornea 13 to be operated upon is positioned prior to operation at a predetermined position with respect to the apparatus. (The positioning system is for projecting images of the slit on the eye to be operated from at least two directions around the optical axis of the observing optical system and performing positioning of the eye based on the positional relation between those slit images projected on the eye. The detail of this positioning system is cited in U.S. Ser. No. 08/090,611 proposed by the same inventor as the present invention.) When it keeps looking a fixed lamp not illustrated, and the eye to be operated is retained in the positioned state.

The apparatus constructed above is wholly controlled through a control device 20. Numeral 21 is a data input device for inputting data of the cornea 13 to be operated upon, including refractive power and the like.

Hypermetropia correcting steps using the apparatus constructed above is next explained. The following description uses a plate made of polymethylmethacrylate (hereinafter called PMMA) instead of a real cornea, the ablation amount (depth) per pulse of which is in a known ratio to that of cornea.

Figure 7:
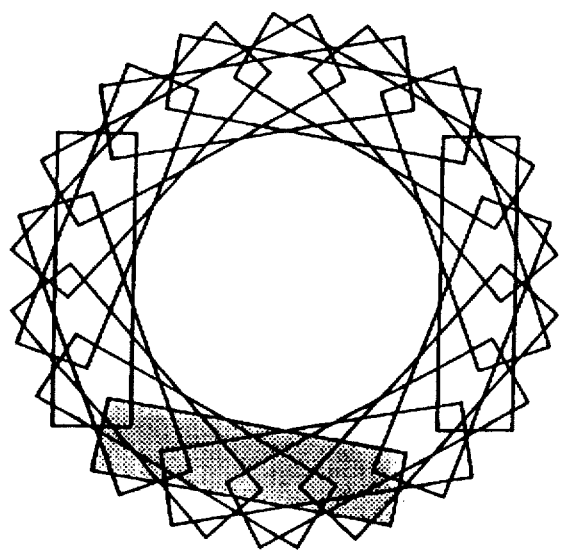
FIG. 7 is an explanatory diagram showing a process to bring an ablation area to a ring profile.

Ablation in a circular profile is first described. The plane mirror 3 is moved by the mirror driving device 4 so as to put the center of a laser beam at a point displaced from the rotation axis L of the image rotator 5. While shifting the irradiation area by rotation of the image rotator 5, the laser beam irradiates successively so as to overlap the ablation area. This profile of the ablation area overlapped may be changed variously from a polygon to an approximate circle according to a combination of the rotation frequency of the image rotator 5 and the repeat frequency of the laser pulse emitted by the laser source 1. It will be unnecessary to consider the combination when a continuous wave (CW) laser is used. When a combination of the rotation frequency and the repeat frequency is suitably chosen, an ablation profile is formed into a ring-shape, referring to FIG. 7.

Figure 8:
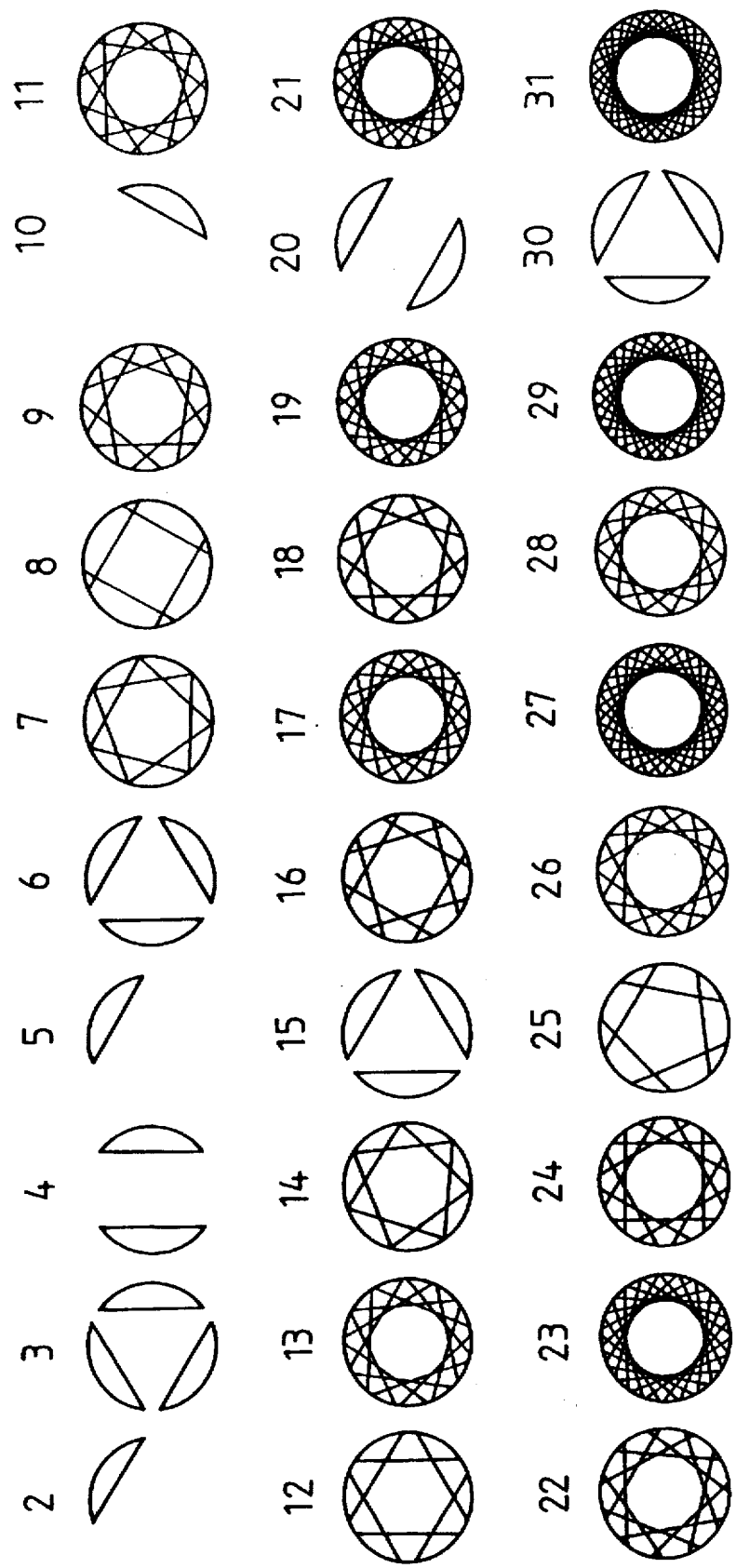
FIG. 8 are patterns taken from the top, which show ablation profiles at each frequency in a case where the laser pulses are superposed while varying its repeat frequency in a range from 2 Hz to 31 Hz.

FIG. 8 shows an ablation profile for each repeat frequency of the laser pulse, the ablation profile being formed by the laser beam where the rotation frequency of the image rotator 5 is determined to 10 Hz and the repeat frequency of the laser pulse is changed in a range of 2 Hz through 31 Hz. From among the combinations above, the following description chooses the use of a combination where the rotation frequency of the image rotator 5 is 10 Hz and the frequency of the laser pulse is 23 Hz. Such a combination of both frequencies is herein used merely for easy control, and it is clear that the frequencies do not need to be fixed as a principle.

Next, the relationship between the displacement distance of the plane mirror 3 to the rotation axis L of the image rotator 5 and depth of ablation is explained.

Figure 10A:
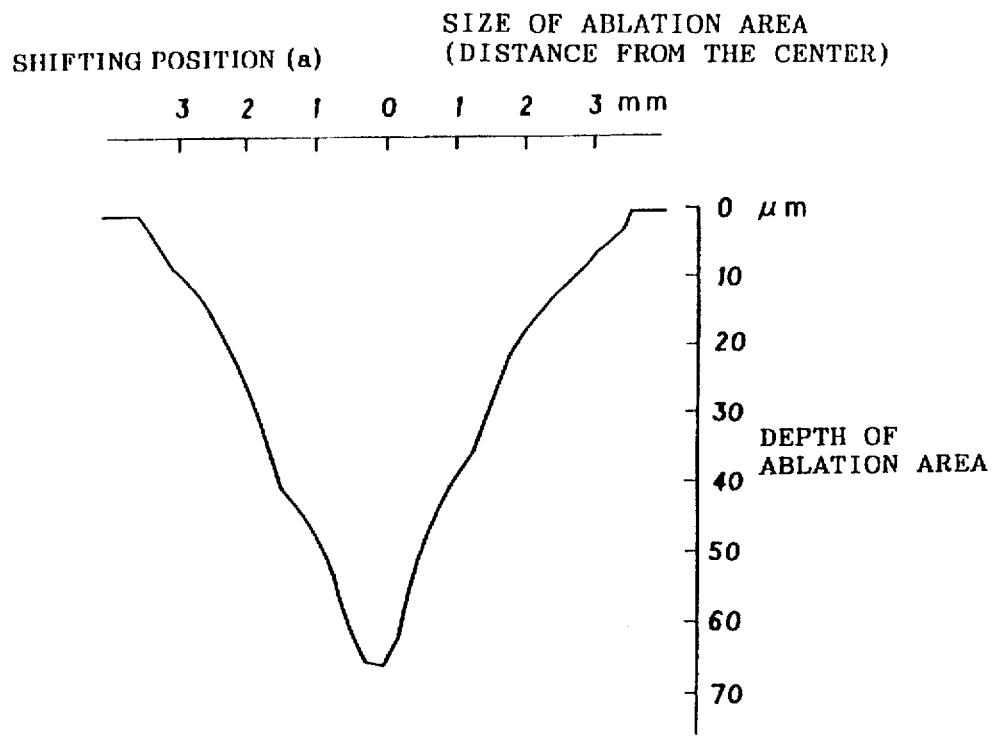
FIGS. 10(a) and (b) are graphs showing the result of ablation when a laser beam is irradiated on a PMMA (polymethylmethacrylate) plate for 30 seconds, the mirror 3 being located at a position (a) and (b) respectively determined in FIG. 9.
Figure 10B:
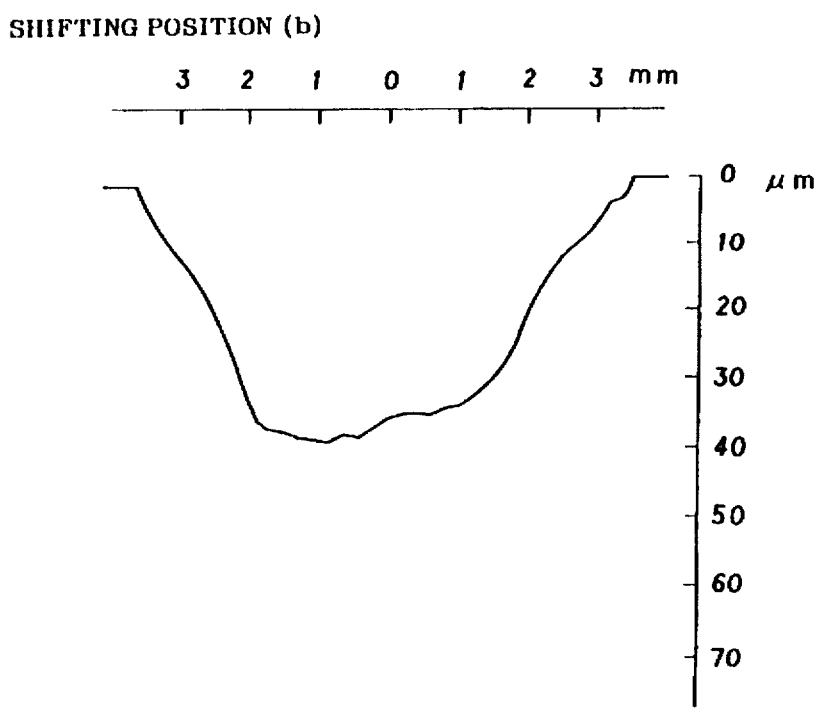
Figure 11:
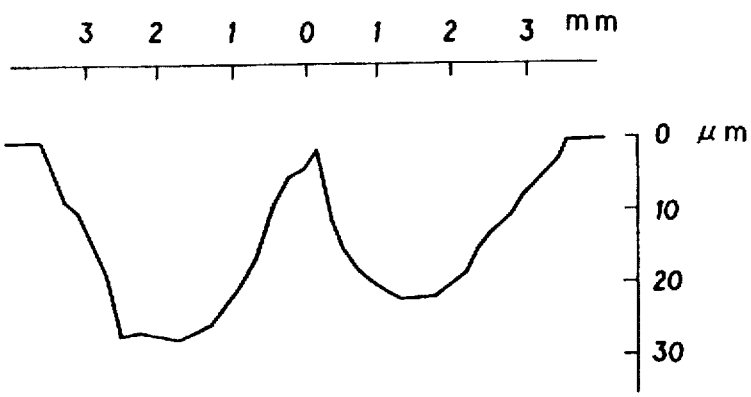
FIGS. 11(c), (d) and (e) are graphs showing the result of ablation when a laser beam is irradiated on a PMMA plate for 30 seconds, the mirror 3 being located at each position (c), (d) and (e) respectively determined in FIG. 9.
Figure 11:
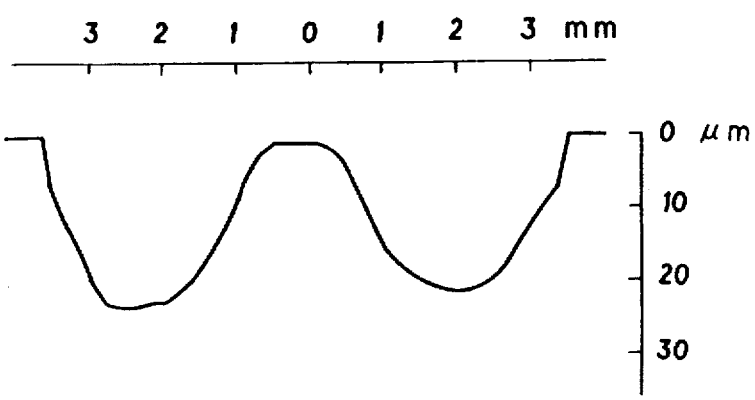
Figure 11:
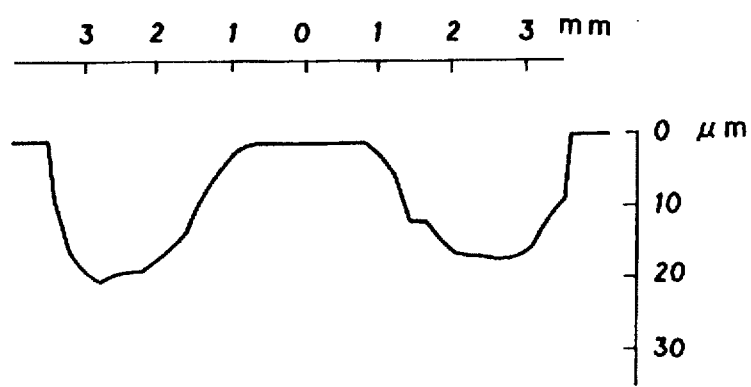
Figure 12F:
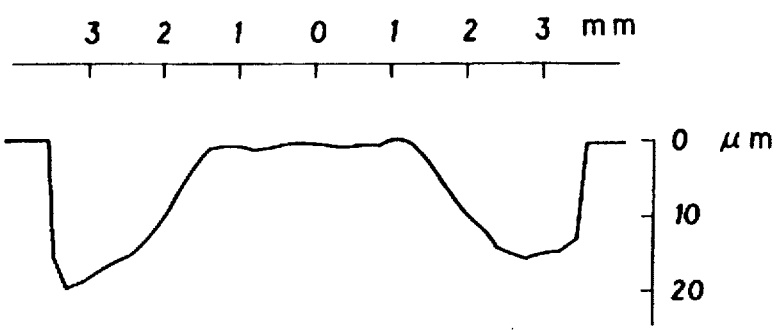
FIGS. 12(f), (g) and (h) are graphs showing the result of ablation when a laser beam is irradiated on a PMMA plate for 30 seconds, the mirror 3 being located at each position (f), (g) and (h) respectively determined in FIG. 9.
Figure 12G:
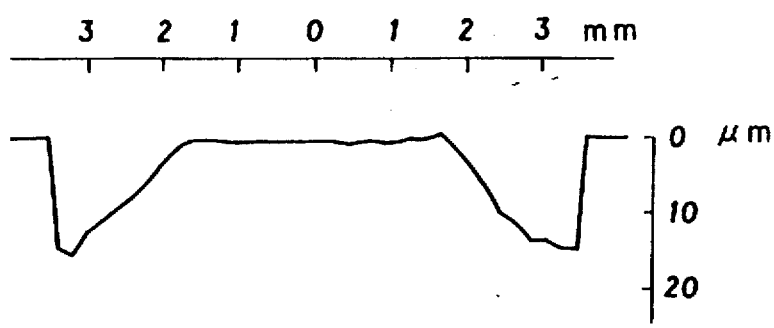
Figure 12H:
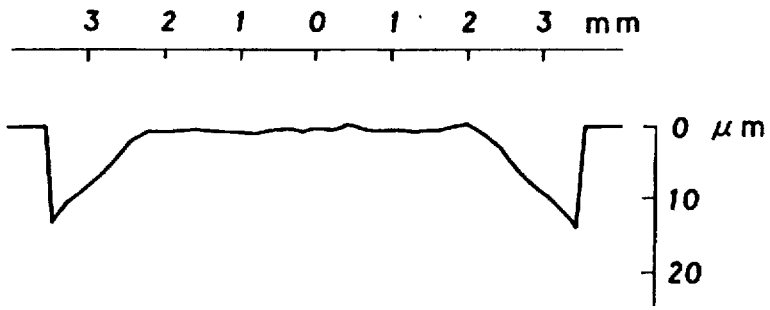
Figure 13:
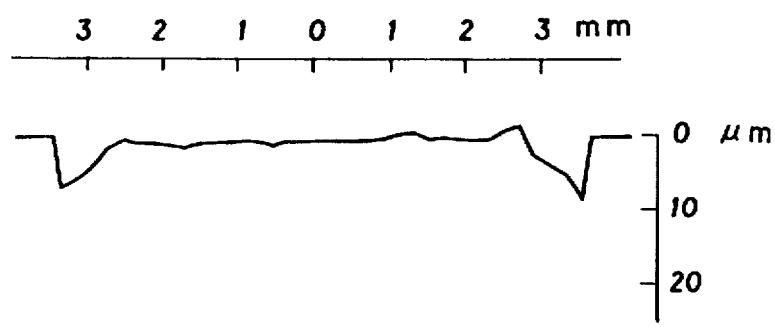
FIG. 13 is a graph showing the result of ablation when a laser beam is irradiated on a PMMA plate for 30 seconds, the mirror 3 being located at a position (i) determined in FIG. 9.

Referring to FIG. 9, the shifting distance of the laser beam from the rotation axis L is determined in nine grades (a) through (i) so as to change every step of 1.4 mm in the range of 1.4 mm–12.6 mm. FIGS. 10 (a) and (b) through FIG. 13 show each result that the PMMA plate is irradiated by the laser beam for 30 seconds at each shifting position (distance). Ablation depth in the present embodiment is simply controlled on the basis of irradiation time, thereby determining the number of pulses, in consideration that the number of irradiation pulses is relatively large to ablation depth per pulse, and also may be controlled based on the number of scans, a scan being the irradiation time (or the number of pulses) per unit, needed for irradiating substantially uniformly a round of an ablation area.

On condition that the irradiation time in each shifting position is equal, the ablation depth becomes deeper at the center of ablation area when a shifting distance of the center of the laser beam from the rotation axis L is small and the ablation area is displaced outward while leaving the center of the ablation area and the ablation depth becomes slighter by degrees because the laser beam is eclipsed more and more by the diaphragm 7 as it is shifted outward.

By combining circular ablation profiles that may be formed in the above way and changing the laser irradiation time (the number of shots) with respect to the shifting distance of the laser beam, the PMMA is ablated into a convex lens shape. FIG. 14 is a table showing an example of combinations of a shifting distance (shifting position) and a ratio of laser beam irradiating time. These combinations are roughly calculated based on depth distribution of cross-sectional profiles shown in FIGS. 10 (a) and (b)—FIG. 13 in order to obtain a refractive power of a certain power. It is possible to obtain different lens powers by changing the total time (the total number of shots) of laser irradiation without changing combinations of each position and the ratio of the laser irradiation time (the number of laser shots). Such lens power was measured with a lensmeter.

FIG. 15 (a) is a table of ablation conditions (1) of when the projective lens 9 is positioned to form an image of the aperture on a cornea. Those ablation conditions A-D vary in the laser irradiation time when high voltage of the laser beam is fixed at 27 KV.

FIG. 15 (b) is a table of ablation conditions (2). In a condition E, the projective lens 9 is moved in the direction denoted by an arrow B and an image of the aperture is magnified to φ9 in diameter. Laser energy is controlled by the control device 20 so as to become 130 mJ at a laser emitting end. In conditions F, G and H, the diameter of the aperture of the diaphragm 7 is reduced to form an ablation image of φ6.5 in diameter, accordingly laser irradiation at a shifting position (i) is omitted.

Figure 17:
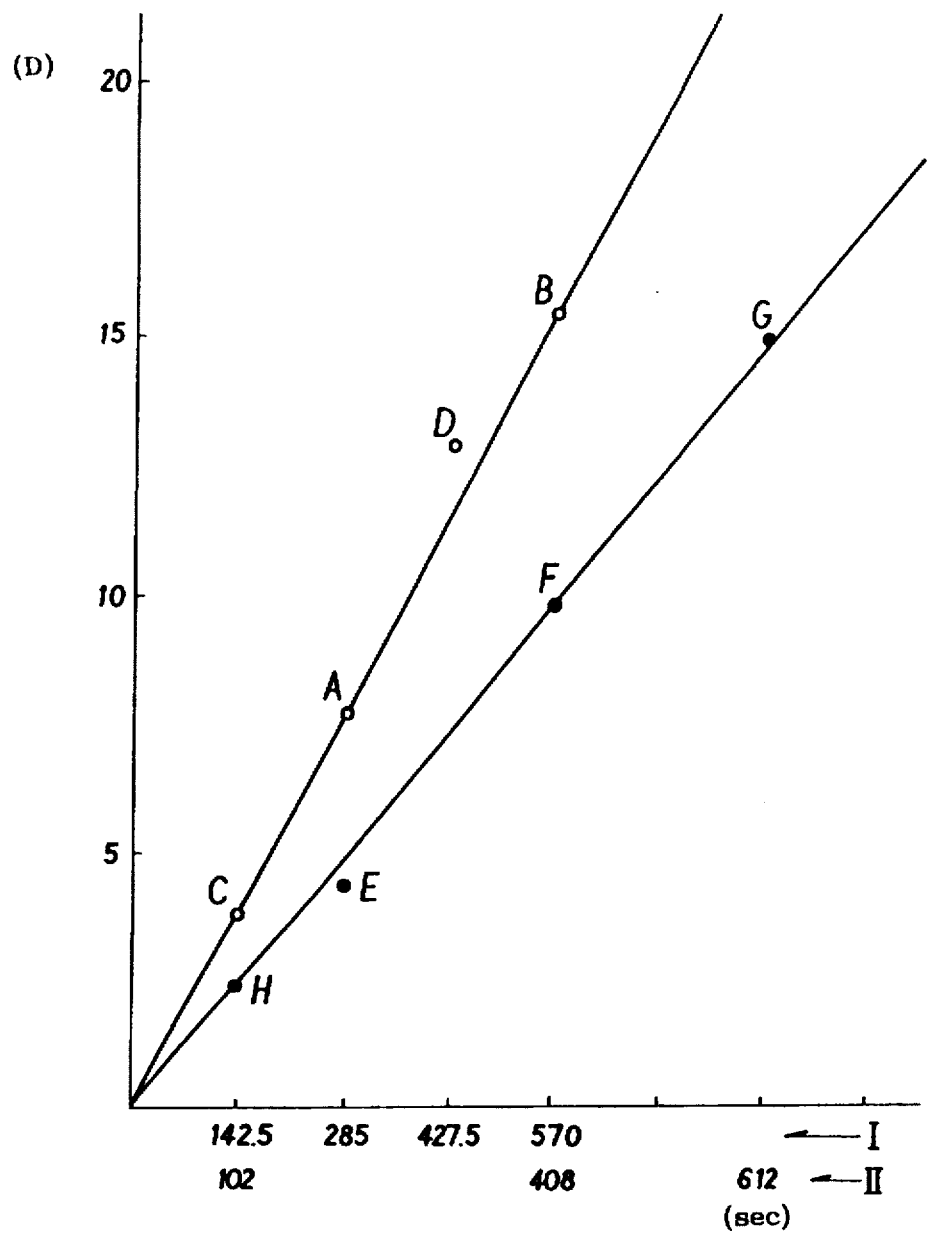
FIG. 17 is a graph corresponding to the data of FIG. 16.

FIG. 16 shows results measured with a lensmeter relating each refractive power of the PMMA plates ablated on the aforementioned conditions. FIG. 17 shows a graph of such results of FIG. 16.

As clearly from FIG. 17, it is understood that ablation conditions A–D in FIG. 15(a) and F, G and H in FIG. 15(b), those conditions being the same except for the laser irradiation time, are mutually related respectively. Refractive power of the PMMA plate to be ablated may be controlled based on the laser irradiation time (the number of pulses).

The control of refractive power may also be applied to a cornea to which ablation depth per pulse is in a known ratio to that of PMMA. When in advance memorizing a table and the like of variation in refractive power to the laser irradiation time (the number of pulses) on a fixed condition of irradiation, and controlling the apparatus based on the table memorized, it is possible to form a cornea of a desired curvature to correct hypermetropia.

Combination of the laser irradiation time at each shifting position is not limited to FIG. 14 and may be changed to other combinations.

In actual operation to correct refractive error, the eye to be operated is located at a predetermined position with respect to the apparatus through an alignment system not illustrated. The apparatus controls movement of the plane mirror 3 through the mirror driving device 4 and time of laser irradiation, based on input information such as a pre-operation cornea shape and a post-operation cornea shape (correcting power) and the like, which is input to the data input device 21, and in accordance with a table of variation of refractive power with respect to the laser irradiation time (the number of pulses). As a result, the eye to be operated is ablated in a desired shape thereby to correct ametropia including hypermetropia.

In the above embodiment of the present invention, by shifting the center of the laser beam by a fixed distance each from the rotation axis and increasing the laser irradiation time (the number of pulses) at each position shifted, the PMMA plate is ablated in a convex lens shape. Alternatively, the PMMA Plate may similarly be ablated in a convex lens shape by controlling the shifting distance of the laser beam from the rotation axis successively providing pulses of laser largely at about the center of the ablation area and smaller as the laser ablates outward.

Figure 1:
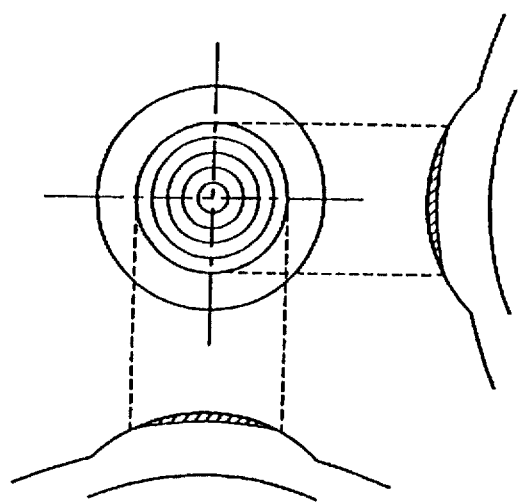
FIGS. 1(a) and (b) are schematic diagrams showing eliminated parts of the cornea of a patient's eye to correct myopia.
Figure 1:
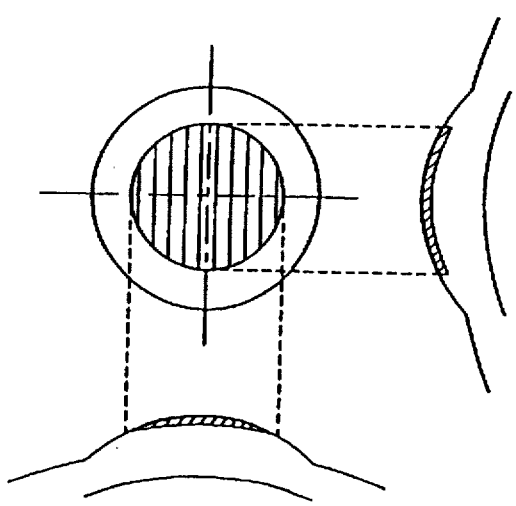

Although the above embodiment is applied for the hypermetropia correction, the present invention may also be applied for a myopia correction. Specifically, as shown in FIGS. 10 (a) and (b), the laser beam rotating ablates the cornea deeply in its center and slighter and slighter as receding from the center. When each position and irradiation time of the laser beam in the center and vicinities (in the vicinity of shifting positions of FIGS. 10 (a)–11 (c)) is controlled to ablate the cornea so as to have a concave surface, the cornea is ablated as shown in FIG. 1 (a) and a myopia correction is consequently achieved. It is possible to control the correction power by varying the laser irradiation time (the total number of shots) as well as the hypermetropia correction.

Next, the operation method for correcting astigmatism will be described hereinafter. Firstly, the method for correcting hypermetropia astigmatism is explained hereinafter. In this case, the PMMA (polymethylmethacrylate) plate is used instead of real cornea.

As described above, the profile of excimer laser beam has an intensity distribution shown in FIG. 6, therefore, when this is irradiated on the PMMA plate, the cross-section where is parallel to x-axis direction of the beams is ablated substantial and uniformly, and the cross-section parallel to y-axis is ablated deepest in its center and slighter and slighter as receding from the center according to a Gaussian intensity distribution F(H). When the number of irradiation pulse (irradiation time) is increased, the ablation depth becomes deeper in proportion to this increase.

Figure 18A:
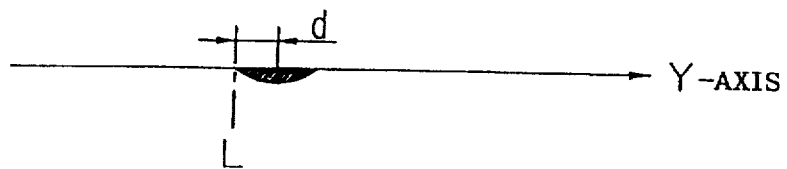
FIGS. 18(a) through 18(d) are explanatory diagram showing an ablation in a case when correcting hypermetropia astigmatism is performed.

In the case that the plane mirror 3 is moved, and the laser is irradiated at the position where the laser beam is shifted in y-axis direction at a certain interval d from the optical axis L of the light delivery optical system, the cross-section parallel to y-axis direction of the plate is ablated as shown in FIG. 18(a).

Figure 18B:
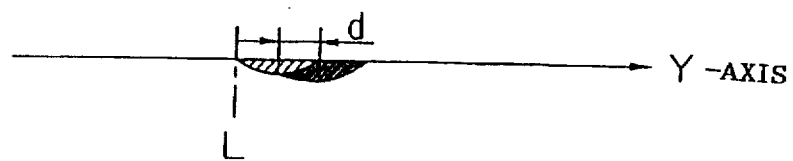
Figure 18C:
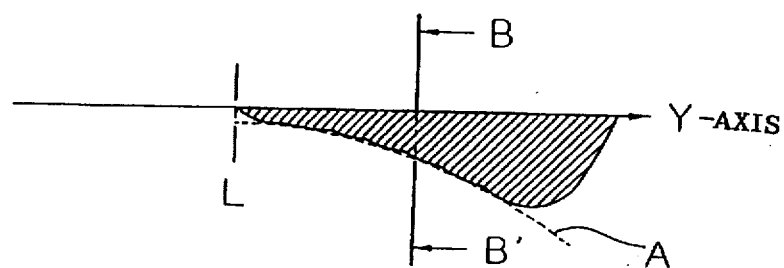
Figure 18D:
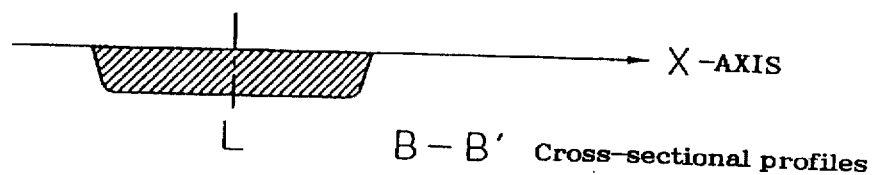

Next, the plane mirror 3 is moved and the number of irradiation laser pulse is much increased at the position where the laser beam is shifted outside of y-axis direction at the further interval d. As the result of this, as shown FIG. 18(b), PMMA plate is ablated more deeply by this laser irradiation than by the first laser irradiation. As like this, by moving of the plane mirror 3, the center of laser beam is moved toward outside of y-axis direction against the optical axis L at every interval d, and the number of laser irradiation pulse is prolonged at each position in proportion as shifting outside, thereon the ablation can be made deep gradually as shown in FIG. 18(c). When the number of laser pulse is increase d by the appropriate ratio at each position, the shape (dotted line A) after the ablation in y-axis direction can be formed as an [ark-shaped]arcuate shape.

On the other hand, although the depth of ablation in x-axis direction is different depending on the positions, the section is ablated like a straight line shape illustrated in FIG. 18 (d). Accordingly, when this ablation is executed in the both sides of y-axis direction about the optical axis L, a surface shape after the ablation can be changed to a cylindrical surface shape (that is, it is possible to ablate like a cylindrical concave lens shape). As another method for ablating in the both sides of y-axis direction against the optical axis L, they are considered that the laser beam is moved by the movement of the plane mirror 3 from one edge of diaphragm to the other edge of that (in the case that the ablation is executed with the image rotator 5 being rotated, it is considered that the plane mirror 3 can be moved by irradiating the laser, which is made to synchronize with the rotation, at every time when the laser beam rotates 360°), or that the movement of the plane mirror 3 and the rotation of the image rotator 5 are combined, and as the laser beam is moved from the center of the light delivery optical system (the optical axis L) to the outside of that (or from the outside to the center) by the movement of the plane mirror 3, the beam is rotated 180° centering the optical axis L (after the one side is completed, the beam is rotated 180° so as that the other side may be carried out, or the alternate ablation can be possible by synchronizing the repetition rate of the laser with the rotating speed of the image rotator 5).

Concerning the control of the degree, similar to the case of the hypermetropia correction described above, without changing the ratio of the number of irradiation pulse (or irradiation time) at each position of the laser beam displaced from the rotation axis L by the movement of the plane mirror 3, the control of the degree can be carried out by changing the whole number of the irradiation pulse (or irradiation time). That is, by making the device store the relation of degree variation (table chart) against the number of laser irradiation pulse under the definite irradiation condition, and then, by controlling the movement of the plane mirror 3 and the number of irradiation pulse are controlled based on this, the cornea can be corrected so as to be the desired shape.

In the case of the operation of correcting hypermetropia astigmatism applied to the above-mentioned ablation method, the tables of degree variation for an aperture diameter of the aperture of diaphragm 7, a rotating angle of the image rotator 5 and a number of irradiation pulse (or laser irradiation time) are read by the control device 20 based on the input information of the pre-operation and the post-operation cornea shape (corrective refractive degree or axial angle) and the like inputted by the data input device 21. And then, according to these data, the control such as the movement of the plane mirror 3, the number of irradiation pulse, and the rotation of image rotator or the like are performed.

Figure 2A:
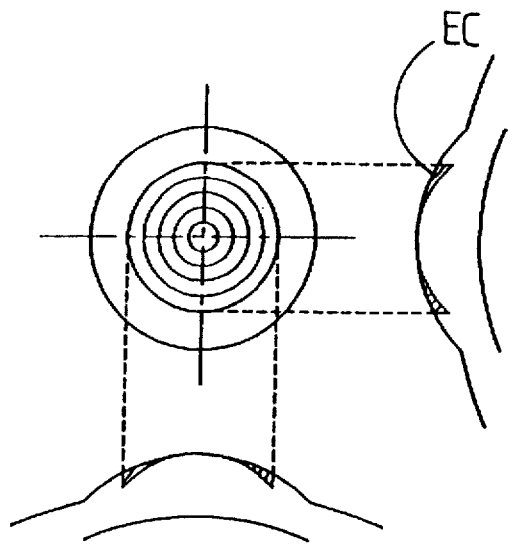
FIGS. 2(a) and (b) are schematic diagrams showing eliminate parts of the cornea of the patient's eye to correct hypermetropia.
Figure 2B:
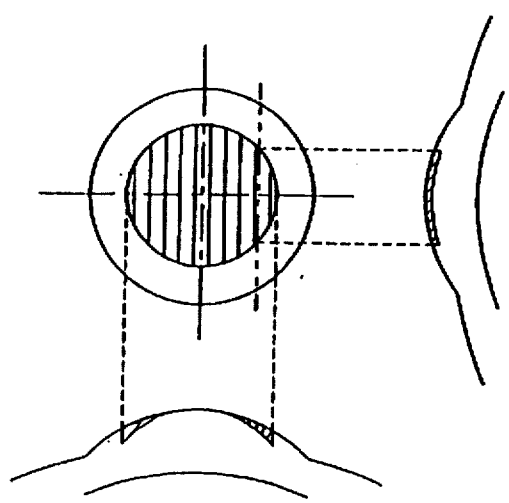
Figure 3:
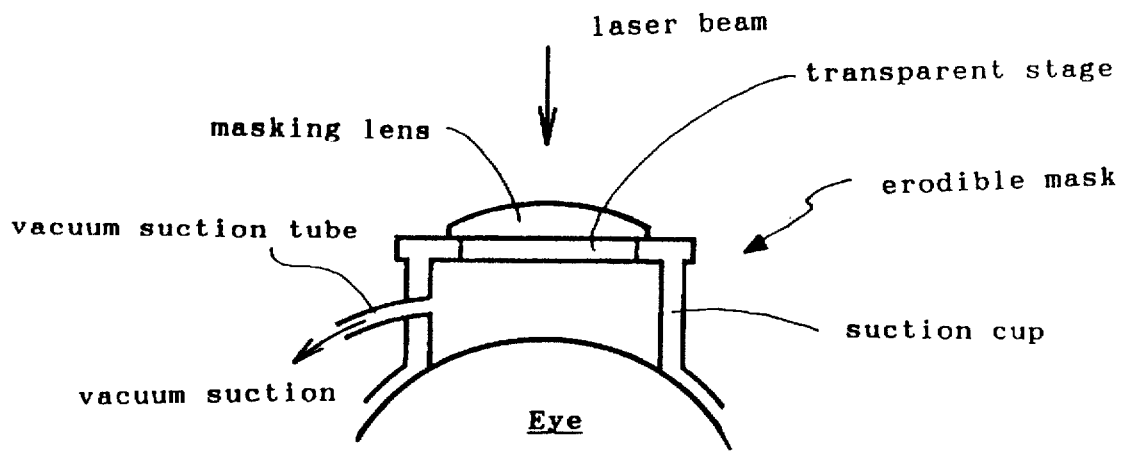
FIG. 3 is a schematic diagram of a mask of the a prior art used for eliminating the surface of the cornea while controlling an aperture to correct hypermetropia.
Figure 4:
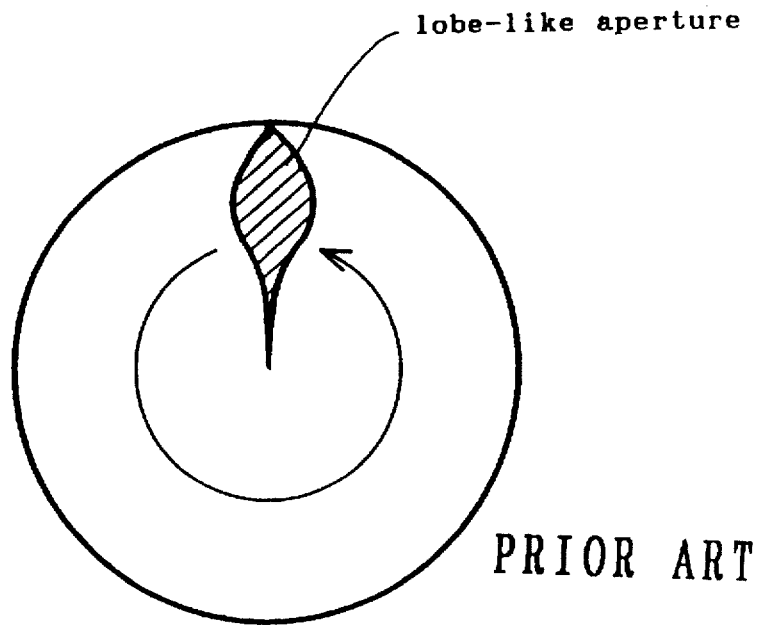
FIG. 4 is a schematic diagram of a lobe-shaped aperture of the prior art used for eliminating the surface of the cornea while controlling an aperture to correct hypermetropia.

The operator locates the eye of the patient at the predetermined position against the apparatus by using an alignment system not illustrated. When the image rotators are rotated so as to adjust the direction, to which the laser beam is moved in parallel, to the axial direction for correcting astigmatism (in the case of the ablation with the image rotator 5 being made to rotate, it is necessary to adjust the position of the laser, which should be irradiated with it being made to synchronize with the rotation of the image rotator 5, to the axial direction for correcting astigmatism), the surface of cornea is ablated according to the table chart, the ablation can be carried out so as to be a cylindrical concave lens-shape as shown in FIG. 2(b), and also the hypermetropia astigmatism correction can be achieved.

As the hypermetropia astigmatism correction is described above, the present invention can be also applied for myopia astigmatism correction as well. In the case of the myopia astigmatism correction, the ratio of the number of irradiation pulses (or irradiation time) at each shifting position in the center of the laser beam against the optical axis L is increased near the center part, and decreased as approaching to the peripheral part, contrary to the hypermetropia astigmatism correction. By the control as described above, the ablation shape as shown FIG. 1(b) can be obtained, and then the cornea operation for correcting myopia astigmatism is achieved.

The present invention may be embodied in other specific forms without departing from the spirit or essential characteristics thereof. For instance, in the preferred embodiment, the ablation is achieved by shifting the laser beam at the regular interval and by changing the number of laser irradiation pulse (irradiation time) so as to be like a cylindrical shape, however it is capable of ablating like a cylindrical shape by maintaining regularly the number of irradiation pulse and by controlling the shifting distance of the laser beam, in the case of the hypermetropia astigmatism, by controlling the shifting distance to be decreased as approaching to the peripheral part, and in the case of the myopia astigmatism correction, by controlling the shifting distance to be increased as approaching to the peripheral part, thereby astigmatism correction can be achieved.

Furthermore, it is capable of performing every ametropia correction by combining it with the spherical correction (hypermetropia, myopia) described in the first preferred embodiment.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The present embodiment is chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An apparatus for use in operating upon a cornea of an eye comprising:

a light delivery optical system for delivering an ultraviolet laser beam emitted from a laser source onto the cornea;

a diaphragm with a variable aperture, disposed in said light delivery optical system, for variably restricting an irradiation area of the laser beam;

means for shifting the laser beam with respect to an optical axis of said light delivery optical system;

means for rotating the laser beam about the optical axis of said light delivery optical system at each shifted position to ablate the cornea circularly;

means for inputting information necessary for determining the shape of a post operative cornea;

means for determining the ablation amount at each shifted position of the laser beam by said beam shifting means, based on the information input through said input means;

means for controlling the laser source and action of the beam rotating means based on the ablation amount determined by said ablation amount determining means at each shifted position; and wherein said laser beam ablates the cornea of the eye to correct ametropia.

2. An apparatus for use in operating a cornea according to claim 1, wherein said ablation amount determining means determines the ablation amount for a hypermetropia correction in which the ablation amount is to increase in proportion to the distance the laser beam is shifted.

3. An apparatus for use in operating upon a cornea according to claim 1, wherein said ultraviolet laser beam is an excimer laser beam.

4. An apparatus for use in operating upon a cornea according to claim 3, wherein the laser beam emitted from said laser source is a pulsed laser beam, and further comprising means for controlling the rotation of the laser beam so that the rotation speed of the laser beam being rotated through the beam rotation means corresponds to a pulse frequency.

5. An apparatus for use in operating upon a cornea according to claim 1, wherein said controlling means controls the irradiation time of the laser beam.

6. An apparatus for use in operating upon a cornea according to claim 4, wherein said controlling means controls the number of pulses of the pulsed laser beam.

7. An apparatus for use in operating upon a cornea according to claim 1, further comprising means for changing the total amount of the ablation area to change hypermetropia correction refractive power while retaining a constant ratio of ablation depth by the laser beam at each shifted position to which the laser beam is shifted by said beam shifting means.

8. An apparatus for use in operating upon a cornea according to claim 1, further including means capable of changing the irradiation area of the laser beam.

9. An apparatus for use in operating upon a cornea to correct ametropia by ablating the cornea with a laser beam comprising:

a light delivery optical system including a movable reflective mirror for delivering an ultraviolet laser beam emitted from a laser source onto a cornea;

a diaphragm with a variable aperture, disposed in said light delivery optical system, for restricting an irradiation area of the laser beam;

means for shifting the laser beam with respect to an optical axis of said light delivery optical system by moving said reflective mirror;

means for rotating the laser beam about the optical axis of said light delivery optical system;

means for inputting information necessary for determining the shape of a post operative cornea;

first memory means for storing the relation between a spherical correction amount and an ablation amount at each shifted position, which amounts are necessary for correcting a spherical refractive power by irradiating and rotating the laser beam about the optical axis of said light delivery optical system at each shifted position to ablate the cornea circularly and accumulate the circular ablation;

second memory means for storing the relation between a cylindrical correction amount and the ablation amount at each shifted position so as to correct the cylindrical refractive power by accumulating the irradiation of the laser beam which is shifted by said beam shifting means, under the condition that the laser beam is rotated by said beam rotating means so that the shifting direction of said shifting means may coincide with the direction of the astigmatism axis;

means for determining the ablation amount at each position of the laser beam based on the input information by said inputting means and said first memory means and said second memory means; and means for controlling movement of the laser source and said beam rotating means at each shifted position based on the ablation amount determined by said ablation amount determining means.

10. An apparatus for use in operating upon a cornea according to claim 9, wherein a cross section of said ultraviolet laser beam is rectangular, the long side direction being substantially uniform, and also the direction perpendicular to the long side of the rectangular cross section having an optical intensity in a Gaussian distribution.

11. An apparatus for use in operating upon a cornea according to claim 10, wherein the laser beam emitted from said laser source is a pulsed laser beam, and said controlling means including the means for rotating and controlling so that the laser beam direction is adjusted to the astigmatism direction by making the pulse frequency of the laser beam correspond to the rotation speed of said beam.

12. An apparatus for use in operating upon a cornea according to claim 9, wherein said beam shifting means comprises a refracting material disposed at said light delivery optical system, and means for moving said refracting material to the direction having an irregular optical intensity of the laser beam.

13. An apparatus for use in operating upon a cornea according to claim 9, wherein said beam shifting means includes means for shifting the laser beam successively at regular intervals.

14. An apparatus for use in operating upon a cornea according to claim 9, wherein said controlling means comprises means for controlling either the irradiation time of the laser beam or the number of pulses based on the ablation amount at each shifted position.

15. An apparatus for use in operating upon a cornea according to claim 9, wherein said controlling means comprises means for controlling the shifting distance by said beam shifting means based on the ablation amount corresponding to the refractive power correction amount under either the regular irradiation time or the number of pulses of the laser beam.

16. An apparatus for use in operating upon a cornea of an eye comprising:

a light delivery optical system for delivering an ultraviolet laser beam emitted from a laser source onto the cornea;

a diaphragm with a variable aperture, disposed in said light delivery optical system, for variably restricting an irradiation area of the laser beam;

means for shifting the laser beam with respect to an optical axis of said light delivery optical system by moving a reflecting mirror of the laser beam;

means for rotating the laser beam about the optical axis of said light delivery optical system at each shifted position to ablate the cornea circularly;

means for inputting information necessary for determining the shape of a post-operative cornea;

means for determining the ablation amount at each shifted position of the laser beam by said beam shifting means, based on the information input through said input means;

means for controlling the laser source and action of the beam rotating means based on the ablation amount determined by said ablation amount determining means at each shifted position; and wherein said laser beam ablates the cornea of the eye to correct ametropia.

17. An apparatus for use in operating upon a cornea according to claim 16, wherein said ablation amount determining means determines the ablation amount for a hypermetropia correction in which the ablation amount is to increase in proportion to the distance the laser beam is shifted.

18. An apparatus for use in operating upon a cornea according to claim 16, wherein said ultraviolet laser beam is an excimer laser beam.

19. An apparatus for use in operating upon a cornea according to claim 18, wherein the laser beam emitted from said laser source is a pulsed laser beam, and further comprising means for controlling the rotation of the laser beam so that the rotation speed of the laser beam being rotated through the beam rotation means corresponds to a pulse frequency.

20. An apparatus for use in operating upon a cornea according to claim 16, wherein said controlling means controls irradiation time of the laser beam.

21. An apparatus for use in operating upon a cornea according to claim 19, wherein said controlling means controls the number of pulses of the pulsed laser beam.

22. An apparatus for use in operating upon a cornea according to claim 16, further comprising means for changing the total amount of the ablation area to change hypermetropia correction refractive power while retaining a constant ratio of ablation depth by the laser beam at each shifted position to which the laser beam is shifted by said beam shifting means.

23. An apparatus for use in operating upon a cornea according to claim 16, further including means capable of changing the irradiation area of the laser beam.

* * * * *

UNITED STATES PATENT AND TRADEMARK OFFICE
CERTIFICATE OF CORRECTION

PATENT NO.: 5,800,424

DATED: September 1, 1998

INVENTOR(S): Toshifumi SUMIYA

It is certified that an error appears in the above-identified patent and that said Letters Patent is hereby corrected as shown below:

Title page, under "Foreign Application Priority Data", change the filing date of Japanese Patent Application HEI 6-166231 from "Jun. 24, 1996" to -- Jun. 24, 1994 --.

Signed and Sealed this

Thirteenth Day of April, 1999

Attest:

Q. TODD DICKINSON

*Attesting Officer*  *Acting Commissioner of Patents and Trademarks*